United States Patent
Lu et al.

(10) Patent No.: US 10,282,631 B2
(45) Date of Patent: May 7, 2019

(54) IMAGE PROCESSING APPARATUS, IMAGE PROCESSING METHOD AND MEDICAL IMAGING DEVICE

(71) Applicant: Toshiba Medical Systems Corporation, Otawara-shi (JP)

(72) Inventors: Jie Lu, Dong Cheng District (CN); Qiqi Xu, Dong Cheng District (CN); Bing Li, Dong Cheng District (CN); Xiaowei Yuan, Dong Cheng District (CN); Kyoko Sato, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/244,043

(22) Filed: Apr. 3, 2014

(65) Prior Publication Data

US 2014/0301621 A1    Oct. 9, 2014

(30) Foreign Application Priority Data

Apr. 3, 2013    (CN) .......................... 2013 1 0115752

(51) Int. Cl.
*G06T 7/33* (2017.01)
*G06K 9/46* (2006.01)
(Continued)

(52) U.S. Cl.
CPC .............. *G06K 9/46* (2013.01); *G06T 7/0002* (2013.01); *G06T 7/337* (2017.01); *A61B 6/507* (2013.01); *G06T 2207/30168* (2013.01)

(58) Field of Classification Search
CPC ......... G06T 2207/20212; G06T 7/0024; G06T 3/0068; H04N 5/23212; A61B 5/7425;
(Continued)

(56) References Cited

U.S. PATENT DOCUMENTS 6,658,080 B1    12/2003 Poole et al.
8,032,202 B2    10/2011 Omi et al.
(Continued)

FOREIGN PATENT DOCUMENTS

JP    4558645 B2    10/2010

OTHER PUBLICATIONS

Abelian, Pascual, Dani Tost, Sergi Grau, and Anna Puig. "Regions-based illustrative visualization of multimodal datasets." Computerized Medical Imaging and Graphics 37, No. 4 (2013): 263-271.*
(Continued)

*Primary Examiner* — Carol Wang
(74) *Attorney, Agent, or Firm* — Oblon, McClelland, Maier & Neustadt, L.L.P.

(57) ABSTRACT

An image processing apparatus, an image processing method and a medical imaging system are disclosed. The image processing apparatus comprises: an original image acquisition section configured to acquire the original image of an object; a parametric image acquisition section configured to acquire a parametric image corresponding to the original image; and an optical attribute value determination section configured to determine, based on the data value of a pixel of the original image and the parameter value of a corresponding pixel in the parametric image, optical attribute values for presenting the pixel of the original image according to a predetermined correspondence.

17 Claims, 6 Drawing Sheets

(51) Int. Cl.
  *G06T 7/00* (2017.01)
  *A61B 6/00* (2006.01)
(58) Field of Classification Search
  CPC ... A61B 6/4417; A61B 6/5229; A61B 6/5235;
       A61B 6/5247; A61B 8/4416; A61B
       8/5238; A61B 8/5261; G02B 21/244
  See application file for complete search history.

(56) References Cited

U.S. PATENT DOCUMENTS

| | | | | |
|---|---|---|---|---|
| 8,472,684 | B1* | 6/2013 | Periaswamy | G06K 9/6289 382/128 |
| 2001/0021794 | A1* | 9/2001 | Muraki et al. | 600/9 |
| 2001/0041835 | A1* | 11/2001 | Front | A61B 6/032 600/429 |
| 2003/0208116 | A1* | 11/2003 | Liang et al. | 600/407 |
| 2003/0234781 | A1* | 12/2003 | Laidlaw et al. | 345/419 |
| 2005/0237328 | A1* | 10/2005 | Guhring | G06T 7/0024 345/520 |
| 2005/0237336 | A1* | 10/2005 | Guhring | G06T 15/08 345/582 |
| 2006/0004275 | A1* | 1/2006 | Vija | A61B 6/00 600/407 |
| 2006/0241402 | A1* | 10/2006 | Ichihara | A61B 6/481 600/425 |
| 2007/0012101 | A1* | 1/2007 | Rottger et al. | 73/170.24 |
| 2007/0014448 | A1* | 1/2007 | Wheeler | G06T 7/0012 382/128 |
| 2007/0036402 | A1* | 2/2007 | Cahill et al. | 382/128 |
| 2007/0049827 | A1* | 3/2007 | Donaldson | A61B 5/0215 600/443 |
| 2007/0098134 | A1* | 5/2007 | Toyoshima et al. | 378/4 |
| 2007/0098299 | A1* | 5/2007 | Matsumoto | G06T 15/08 382/284 |
| 2008/0055305 | A1* | 3/2008 | Blank | G06T 15/08 345/419 |
| 2008/0114234 | A1* | 5/2008 | Gering | 600/411 |
| 2009/0063118 | A1* | 3/2009 | Dachille | G06F 17/30262 703/11 |
| 2010/0106002 | A1* | 4/2010 | Sugiyama et al. | 600/410 |
| 2010/0286517 | A1* | 11/2010 | Kamen et al. | 600/438 |
| 2011/0152671 | A1* | 6/2011 | Aime | G01R 33/5601 600/420 |
| 2012/0019548 | A1* | 1/2012 | Zhu | G06T 11/001 345/589 |
| 2012/0038649 | A1* | 2/2012 | Kanitsar et al. | 345/440 |
| 2012/0076387 | A1 | 3/2012 | Hu | |
| 2012/0249743 | A1* | 10/2012 | Kim | H04N 5/23293 348/46 |
| 2013/0261429 | A1* | 10/2013 | Lee | A61B 5/055 600/411 |
| 2014/0180060 | A1* | 6/2014 | Parrish | G01R 33/4806 600/411 |
| 2016/0055634 | A1* | 2/2016 | Bystrov | G06T 5/50 382/128 |

OTHER PUBLICATIONS

Haidacher, Martin, Stefan Bruckner, Armin Kanitsar, and M. Eduard Gröller. "Information-based transfer functions for multimodal visualization." In VCBM, pp. 101-108. 2008.*
Kniss, Joe, Gordon Kindlmann, and Charles Hansen. "Multidimensional transfer functions for interactive volume rendering." IEEE Transactions on visualization and computer graphics 8, No. 3 (2002): 270-285.*
Combined Office Action and Search Report dated May 26, 2016 in Chinese Patent Application No. 201310115752.8 (with English language translation).
Office Action dated Jan. 9, 2018, in Japanese Patent Application No. 2014-076438.

* cited by examiner

IMAGE PROCESSING APPARATUS, IMAGE PROCESSING METHOD AND MEDICAL IMAGING DEVICE

CROSS-REFERENCE TO RELATED APPLICATIONS

This application is based upon and claims the benefit of priority from Chinese Patent Application No. 201310115752.8, filed on Apr. 3, 2013, the entire contents of which are incorporated herein by reference.

FIELD

The present invention relates to image processing and more particularly to an image processing apparatus and an image processing method for determining image presentation parameters and a medical imaging device comprising the image processing apparatus.

BACKGROUND

The original image of an object obtained by various imaging methods is actually a data field of specific data (e.g. a two-dimensional data field or three-dimensional data field). After being obtained, the original image needs to be presented (that is, visualized), for example, on a two-dimensional image or screen to achieve an intuitive visualization result.

Existing image presentation methods (e.g. volume rendering) acquire image presentation parameters by performing calculation on the data of the original image.

BRIEF DESCRIPTION OF THE DRAWINGS

The present invention will be better understood with reference to the following description taken in conjunction with accompanying drawings in which identical or like reference signs designate identical or like components. The accompanying drawings, together with the detailed description below, are incorporated into and form a part of the specification and serve to illustrate, by way of example, preferred embodiments of the present invention and to explain the principle and advantages of the present invention. In the accompanying drawings.

DETAILED DESCRIPTION

A brief summary of the present invention is given below to provide a basic understanding of some aspects of the present invention. It should be appreciated that the summary is not an exhaustive overview of the present invention, is not intended to identify the key or critical parts of the present invention nor to limit the scope of the present invention, but merely to present some concepts in a simplified form as a prelude to the more detailed description that is discussed later.

In accordance with an aspect of the present invention, an image processing apparatus comprises: an original image acquisition section configured to acquire the original image of an object; a parametric image acquisition section configured to acquire a parametric image corresponding to the original image; and an optical attribute value determination section configured to determine, based on the data value of a pixel of the original image and the parameter value of a corresponding pixel in the parametric image, optical attribute values for presenting the pixel of the original image according to a predetermined correspondence.

In accordance with another aspect of the present invention, an image processing method comprises: acquiring the original image of an object; acquiring a parametric image corresponding to the original image; and determining, based on the data value of a pixel of the original image and the parameter value of a corresponding pixel in the parametric image, optical attribute values for presenting the pixel of the original image according to a predetermined correspondence.

In accordance with still another aspect of the present invention, there is provided a medical imaging device which comprises the aforementioned image processing apparatus.

In accordance with yet another aspect of the present invention, a program product is provided in which machine-readable instruction codes are stored. When read and executed by a computer, the instruction codes enable the computer to execute the image processing method disclosed herein or to serve as the image processing apparatus disclosed herein.

In accordance with yet still another aspect of the present invention, a storage medium is provided in which a program product is carried in which the machine-readable instruction codes are stored.

Preferred embodiments of the present invention are described below with reference to accompanying drawings. The elements and features described in one accompanying drawing or one embodiment of the present invention may be combined with those shown in one or more other accompanying drawings or embodiments. It should be noted that for the sake of clarity, the representation and description of the components and processing that are irrelative with the present invention and well known by those skilled in the art are omitted.

Figure 1:
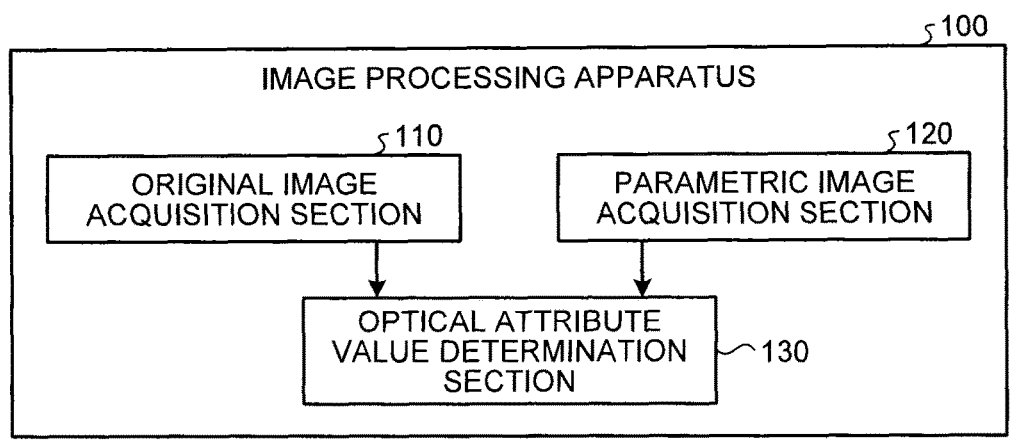
FIG. 1 is a block diagram illustrating an exemplary configuration of an image processing apparatus according to an embodiment of the present invention.

As shown in FIG. 1, the image processing apparatus 100 according to an embodiment of the present invention comprises an original image acquisition section 110, a parametric image acquisition section 120 and an optical attribute value determination section 130.

The original image acquisition section 100 is configured to acquire the original image of an object. For instance, the original image acquisition section 100 may acquire the image obtained by, but not limited to: magnetic resonance imaging (MRI), X-ray imaging, ultrasonic (UL) imaging, computed tomography (CT) imaging or positron emission tomography (PET) imaging.

The parametric image acquisition section 120 is configured to acquire a parametric image corresponding to the original image acquired by the original image acquisition section 100.

The parametric image may include a function image with a specific meaning which is calculated from the original image using a certain algorithm. For instance, if the original image is a magnetic resonance image, the corresponding parametric image may include but is not limited to: a chemical shift image (CSI); a diffusion-weighted image (DWI); a cerebral blood volume (CBV) image, a cerebral blood flow (CBF) image, a mean transit time (MTT) image, an area under the curve (AUC) image, a peak height (PH) image of concentration curve, a time to peak (PT) image and a transit time (TT) image imaged by perfusion-weighted imaging (PWI); an apparent diffusion coefficient (ADC) image, an isotropic apparent diffusion coefficient (Iso-ADC) image, a fractional anisotropy (FA) image, a relative anisotropy (RA) image, a volume ratio (VR) image imaged by diffusion tensor imaging (DTI) or diffusion tensor tractography (DTT); a blood oxygen-level dependent (BOLD) image; a Map image imaged by magnetic resonance elastography (MRE) and a Map image imaged by amide proton transfer (APT) imaging; a T1 map image; T2 map image; T2*(T2 star) map image.

Alternatively, the parametric image may include a corresponding image obtained by an imaging method different from that of the original image. For instance, the original image and the parametric image may be obtained by two different imaging methods among the aforementioned imaging methods.

Further, it should be noted that the original image acquisition section 110 and the parametric image acquisition section 120 may generate the original image and the parametric image by themselves or receive from another apparatus, for example, an imaging apparatus or a calculation apparatus, the original image and the parametric image generated by the another apparatus.

The optical attribute value determination section 130 is configured to determine, based on the data value of a pixel of the original image and the parameter value of a corresponding pixel in the parametric image, optical attribute values for presenting the pixel of the original image according to a predetermined correspondence.

The term 'pixel', as used herein, may include the pixel of a two-dimensional image, or the pixel of a three-dimensional image, that is, voxel.

For example, the optical attributes for presenting the pixel may include, but is not limited to: color (e.g. represented by RGB or YUV values), grayscale or transparency (a value), etc.

The parameter value of the parametric image may provide the information that cannot be directly reflected by the data of the original image. For instance, in the case where the parametric image is a function image calculated from the original image using a certain algorithm, the parameter value in the parametric image is capable of indicating a specific attribute of a corresponding part in the original image. Further, if the parametric image is an image obtained by an imaging method different from that of the original image, owing to the features of different imaging methods, the parametric image may provide specific information absent in the original image.

Thus, the image processing apparatus 100 according to an embodiment of the invention determines optical attribute values for presenting the original image based on both the data value of the original image and the parameter value of the parametric image, which enables the combination of the additional information of the parametric image with the original image to present the original image more targetedly. For instance, a region of interest determined based on the parametric image may be highlighted in the original image to achieve a better presentation effect.

Figure 2:
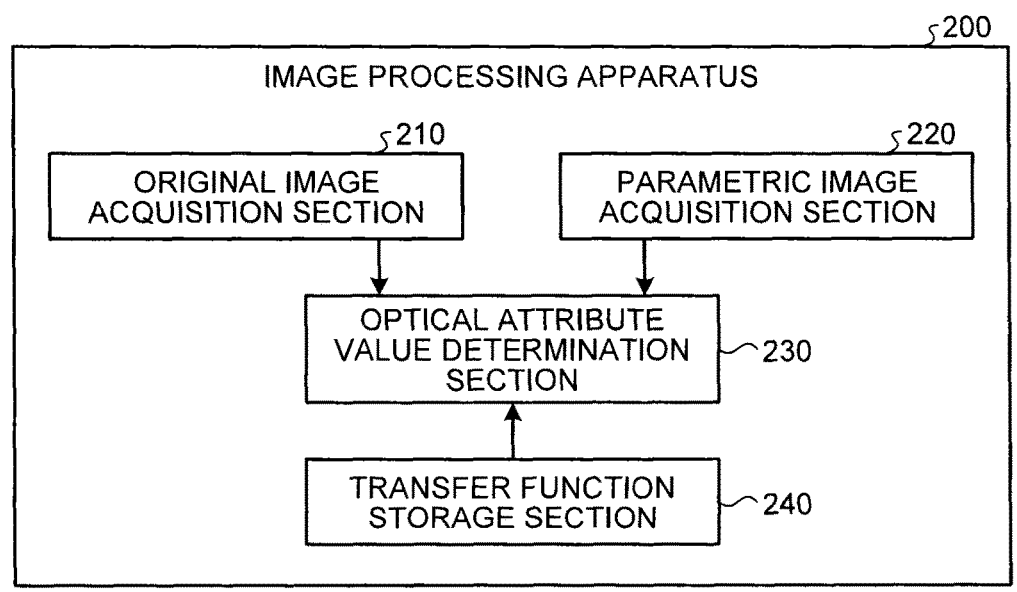
FIG. 2 is a block diagram illustrating an exemplary configuration of an image processing apparatus according to another embodiment of the present invention.

According to an embodiment of the present invention, the predetermined correspondence between the data value of the original image and the parameter value of the parametric image and an optical attribute value may be defined by a transfer function. As shown in FIG. 2, an image processing apparatus 200 according to an embodiment of the present invention comprises an original image acquisition section 210, a parametric image acquisition section 220, an optical attribute value determination section 230 and a transfer function storage section 240.

Similarly configured as the original image acquisition section 110 and the parametric image acquisition section 120 that are described above with reference to FIG. 1, the original image acquisition section 210 and the parametric image acquisition section 220 are not repeatedly described here. The transfer function storage section 240 is configured to store a transfer function for defining a correspondence according to which the optical attribute value determination section 230 determines optical attribute values, wherein the transfer function takes the data value of the original image and the parameter value of the parametric image as input and the optical attribute values for presenting a corresponding pixel as output. For instance, assuming that optical attribute values include a color value and a transparency value, then the transfer function may include the following form: RGBA=f(data, para), wherein "data" represents the data value of the pixel of the original image, "para" represents the parameter value of a corresponding pixel in the parametric image, and the color value (RGB components) and a transparency value (α value) can be determined according to the data value and the para value. The specific form of the transfer function can be set as needed.

According to an embodiment of the present invention, the optical attribute value determination section can be configured to determine, for at least one optical attribute, that an area in the original image corresponding to a specific parameter value range has a specific optical attribute value so as to distinguish the area. For instance, pixels having parameter value in a specific range can be set to have a specific color, or pixels having parameter value in a specific range can be set to have a specific transparency.

Figure 3:
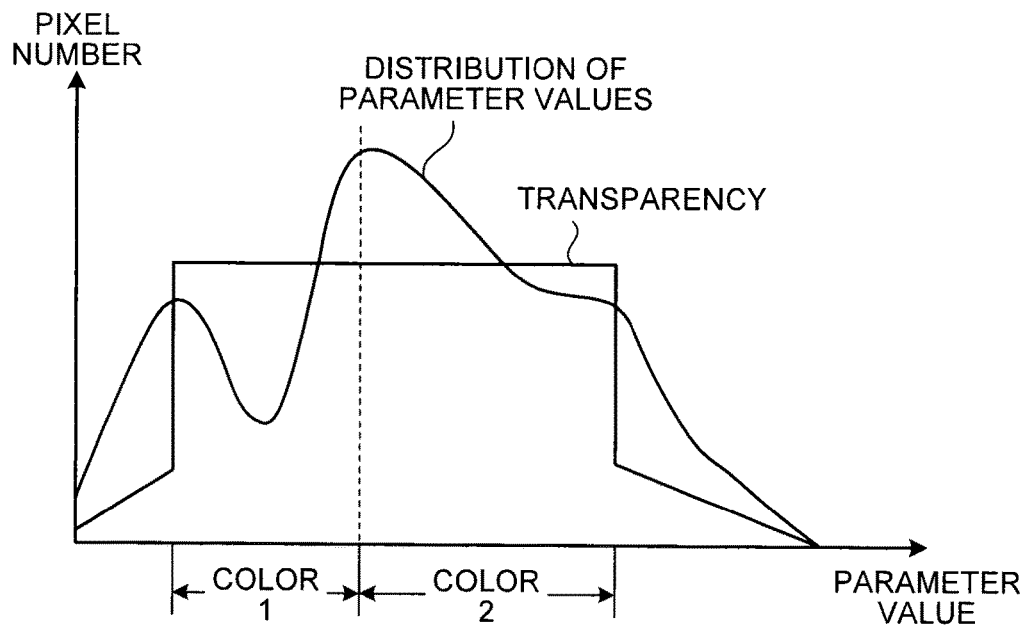
FIG. 3 shows an exemplary correspondence according to which the optical attribute value determination section of an image processing apparatus disclosed herein determines optical attribute values based on parameter values.

FIG. 3 shows an example of the predetermined correspondence. In FIG. 3, the curve indicated by "distribution of parameter values" represents the distribution of the parameter values of the pixels in the parametric image. When the original image is presented, the pixels corresponding to the parameter range indicated by "color 1" are set to have a first color and the pixels corresponding to the parameter range indicated by "color 2" are set to have a second color. Thus, pixels corresponding to different parameter value ranges are distinguished by being set with different colors. Further, the curve indicated by "transparency" represents the transparency setting of pixels, in the example, the pixels corresponding to the parameter ranges indicated by "color 1" and "color 2" are set to have a higher transparency value (that is, being relatively non-transparent) so as to highlight the pixels.

For instance, assuming that the original image is a magnetic resonance (MR) image (e.g. a T1W image), if the parametric image is a fractional anisotropy (FA) image, then the optical attribute value determination section may determine optical attribute values to highlight or differentially display an area corresponding to the parameter value of grey matter or white matter; if the parametric image is a chemical shift image (CSI), the optical attribute value determination section may determine optical attribute values to highlight an area corresponding to the parameter value of a tumor area; and if the parametric image is a diffusion-weighted image (DWI), the optical attribute value determination section may determine optical attribute values to highlight an area corresponding to the parameter value of a cerebral infarction area. However, the present invention is not limited to the specific examples listed above, and the optical attribute values for presenting the original image may be set using other parametric images according to various correspondences to display various regions of interest differentially.

Further, the optical attribute value determination section can be configured to determine, in an area in the original image corresponding to the same parameter value range, a specific optical attribute value for a sub-area corresponding to a specific data value range of the original image so as to distinguish the sub-area.

Figure 4:
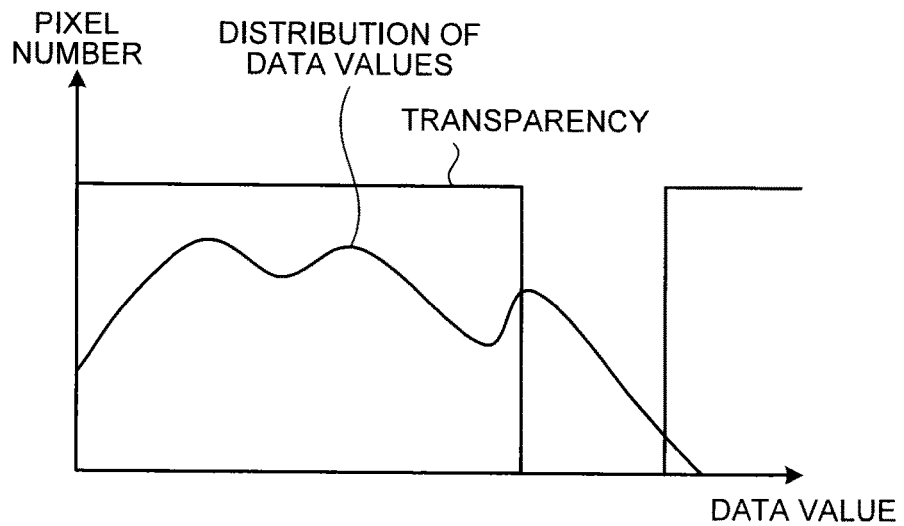
FIG. 4 shows an exemplary correspondence according to which the optical attribute value determination section of an image processing apparatus disclosed herein determines optical attribute values based on data values of an original image.

For instance, as shown in FIG. 4, the curve indicated by "distribution of data values" represents the distribution of the data values of the pixels of the original image corresponding to the same parameter value range (e.g. the parameter range indicated by "color 1" or "color 2" in FIG. 3). In this case, although that portion of pixels are determined to have the same color, the pixels having specific data values may be set to be transparent using the sag part of the curve "transparency", thereby filtering out the part from the image presented.

For instance, if the original image is a magnetic resonance image (e.g. a T1W image) and the parametric image is a fractional anisotropy (FA) image, for the pixels having parameter values in the same range, the pixels corresponding to a given original image data value range (e.g. a data value range corresponding to skeleton) may be set to be transparent to present the other parts in the original image better. Apparently, the present invention is not limited to the specific example above.

Figure 5:
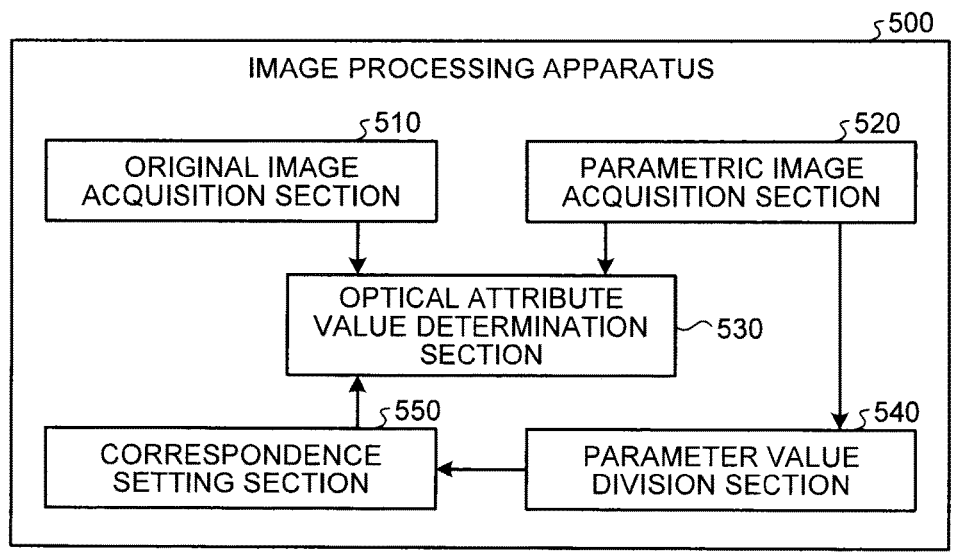
FIG. 5 is a block diagram illustrating an exemplary configuration of an image processing apparatus according to an embodiment of the present invention.

Further, there may be a case where there are a plurality regions of interest in an imaging range and each region of interest is desired to be highlighted separately. Correspondingly, as shown in FIG. 5, an image processing apparatus 500 according to an embodiment of the present invention comprises an original image acquisition section 510, a parametric image acquisition section 520, an optical attribute value determination section 530, a parameter value division section 540 and a correspondence setting section 550.

Similarly configured as the original image acquisition section and the parametric image acquisition section described in the aforementioned embodiments, the original image acquisition section 510 and the parametric image acquisition section 520 are not repeatedly described here. The parameter value division section 540 is configured to divide the parameter values of the parametric image acquired by the parametric image acquisition section 520 into two or more ranges, each of which corresponds to a different region of interest. The correspondence setting section 550 is configured to set a correspondence individually for each parameter value range to enable the optical attribute value determination section 530 to determine optical attribute values for differentially presenting an area corresponding to the parameter value range according to the correspondence set by the correspondence setting section 550. That is, a plurality of correspondences may be set for the same kind of parametric image, wherein each correspondence can be used to highlight a corresponding region of interest. Further, the correspondence set by the correspondence setting section 550 may be stored in a storage section (not shown) so that the preset correspondence can be directly acquired from the storage section when a region of interest is to be presented.

Figure 6:
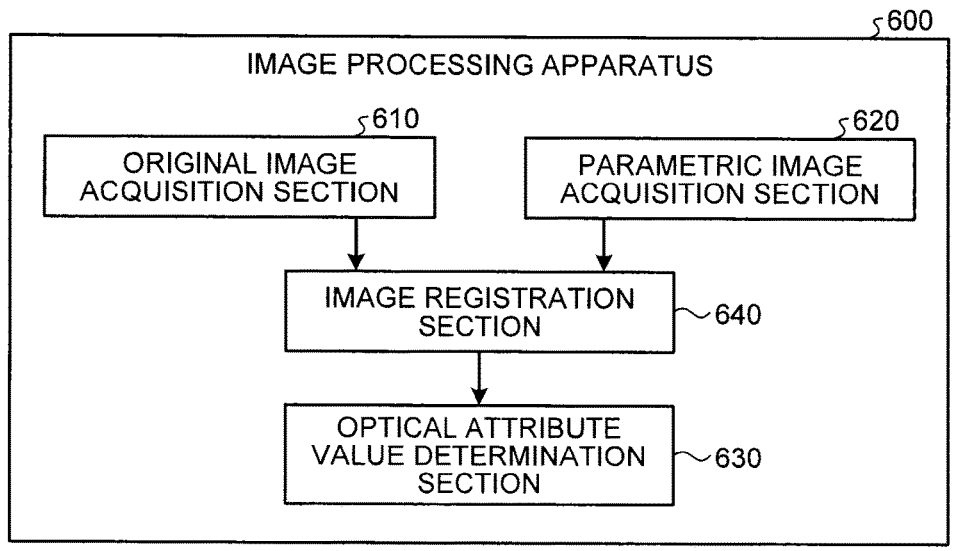
FIG. 6 is a block diagram illustrating an exemplary configuration of an image processing apparatus according to another embodiment of the present invention.

Further, in a case where the boundaries of the original image and the parametric image are not matched with each other, an image registration may be carried out to determine corresponding pixels in the original image and the parametric image. As shown in FIG. 6, an image processing apparatus 600 according to an embodiment of the present invention comprises an original image acquisition section 610, a parametric image acquisition section 620, an optical attribute value determination section 630 and an image registration section 640. The configurations of the original image acquisition section 610, the parametric image acquisition section 620 and the optical attribute value determination section 630 are similar as the original image acquisition section, the parametric image acquisition section and the optical attribute value determination section described in the aforementioned embodiments. The image registration 640 is configured to perform an image registration to determine corresponding pixels in the original image and the parametric image. The image registration section 640 may perform the image registration in a plurality of specific known ways that are not described here in detail.

Incidentally, the original image and the parametric image may have different resolutions. For instance, the resolution of the original image may be higher than that of the parametric image. In this case, a plurality of adjacent pixels in the original image may correspond to the same pixel in the parametric image. Correspondingly, the optical attribute values of the plurality of pixels in the original image can be determined according to the parameter value of the pixel in the parametric image and the data values of the plurality of pixels in the original image. Similarly, the resolution of the parametric image may be higher than that of the original image. In this case, a plurality of adjacent pixels in the parametric image may correspond to the same pixel in the original image. Correspondingly, the optical attribute values of the pixel in the original image can be determined according to the data value of the pixel in the original image and the parameter values of the plurality of pixels in the parametric image.

It is apparent that some processing or methods are also disclosed in the aforementioned description of the image processing apparatus. Summaries of the methods will be described hereinafter without repeating the details discussed above. However, it should be noted that although the methods are disclosed in the description of the image processing apparatus, the methods do not necessarily employ the aforementioned components or are not necessarily executed by the aforementioned components. For instance, embodiments of the image processing apparatus may be partially or completely achieved by hardware and/or firmware. However, the image processing method described below can be fully achieved by a computer-executable program, although they can also be executed by the hardware and/or firmware of the image processing apparatus.

Figure 7:
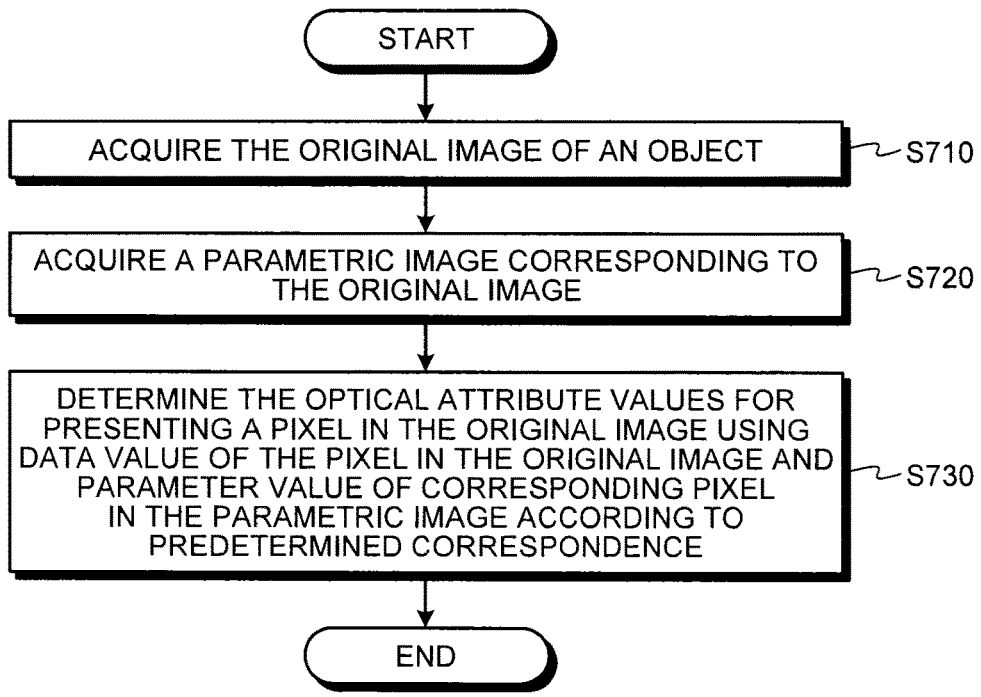
FIG. 7 is a flowchart showing an exemplary processing of an image processing method according to an embodiment of the present invention.

As shown in FIG. 7, in an image processing method according to an embodiment of the present invention, the original image of an object is acquired in Step S710. In step S720, a parametric image corresponding to the original image is acquired.

As stated above, the original image may be an image obtained by but not limited to: magnetic resonance imaging, X-ray imaging, ultrasonic imaging, computed tomography imaging or positron emission tomography imaging. The parametric image may be obtained by performing numerical calculation on the original image (for example, the aforementioned parametric images corresponding to a magnetic resonance image), or obtained by an imaging method different from that of the original image. Further, acquiring the original image or parametric image may include directly obtaining the original image or parametric image using an imaging method or a calculation method. Alternatively, acquiring the original image or parametric image may also include receiving the generated original image or parametric image from a peripheral device.

In Step S730, optical attribute values for presenting a pixel in the original image are determined using the data value of the pixel in the original image and the parameter value of a corresponding pixel in the parametric image according to a predetermined correspondence. The optical attributes include, for example, color, grayscale or transparency. The correspondence may be defined using a transfer function which takes the data value of the original image and the parameter value of the parametric image as input and the optical attribute values for presenting the original image as output.

Figure 8:
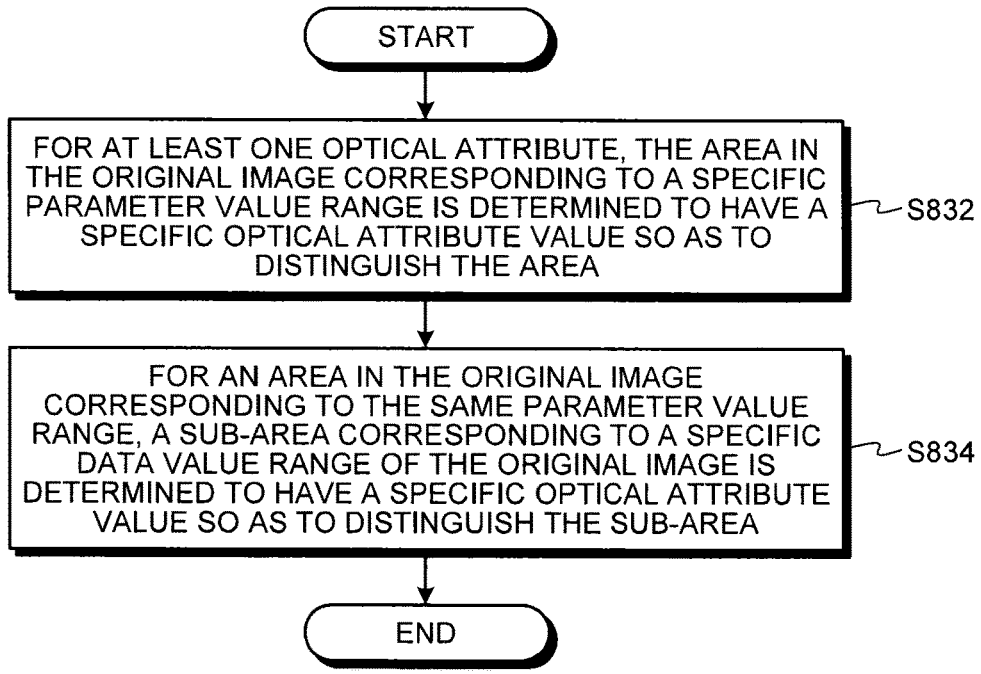
FIG. 8 is a flowchart showing an exemplary processing of optical attribute determination in an image processing method according to an embodiment of the present invention.

The step of determining optical attribute values according to a predetermined correspondence may include the processing shown in FIG. 8. In Step S832, for at least one optical attribute, an area in the original image corresponding to a specific parameter value range is determined to have a specific optical attribute value so as to distinguish the area. Thus, a region of interest in the original image can be presented differentially according to the parametric image. For instance, assuming that the original image is a magnetic resonance image, when the parametric image is a fractional anisotropy image, optical attribute values may be determined to highlight or differentially display an area corresponding to the parameter value of grey matter or white matter; when the parametric image is a chemical shift image, optical attribute values may be determined to highlight an area corresponding to the parameter value of a tumor area; and when the parametric image is a diffusion-weighted image, optical attribute values may be determined to highlight an area corresponding to the parameter value of a cerebral infarction area. However, the present invention is not limited to the specific example listed above. Further, in an area in the original image corresponding to the same parameter value range, a specific optical attribute value can be determined for a sub-area corresponding to a specific data value range of the original image so as to distinguish the sub-area, as shown in Step S834. Thus, different parts of an area corresponding to the same parameter value range are presented differentially according to the data value of the original image. For instance, if the original image is a magnetic resonance image and the parametric image is a fractional anisotropy image, for the pixels the parameter values of which are in the same range, the pixels corresponding to the data value range of the original image corresponding to, e.g., skeleton may be set to be transparent, thereby presenting the other parts in the original image better. However, the present invention is not limited to the specific example above.

Figure 9:
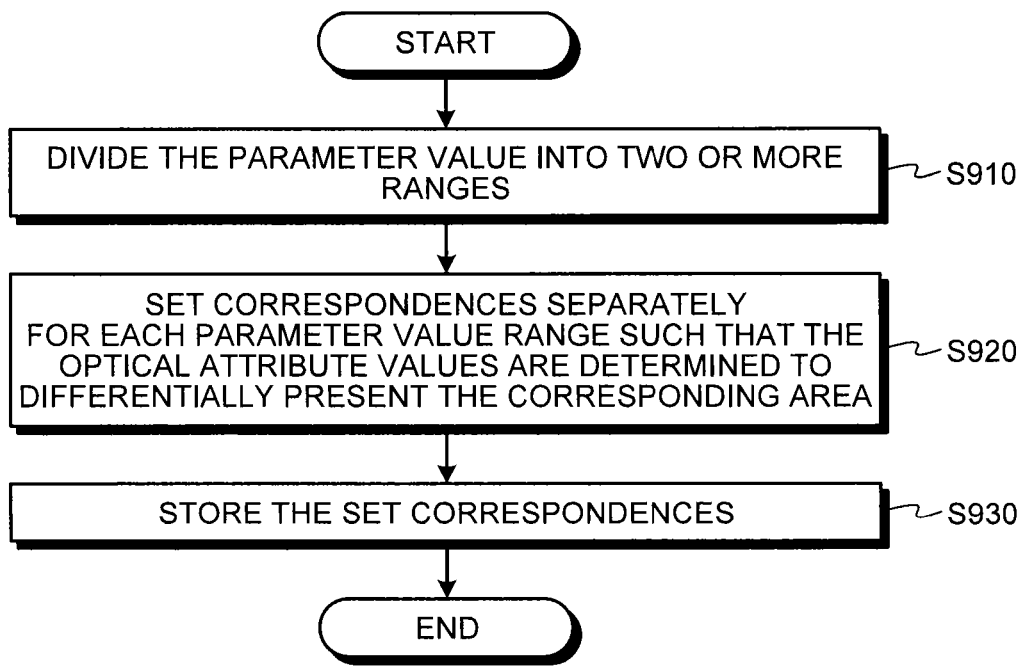
FIG. 9 is a flowchart showing an exemplary processing for setting a plurality of correspondences in an image processing method according to an embodiment of the present invention.

Further, in presenting a plurality of regions of interest differentially, the method according to an embodiment of the invention may further include the processing shown in FIG. 9. In Step S910, the parameter value may be divided into two or more ranges, each of which can correspond to an individual region of interest. In Step S920, correspondences for determining the optical attribute are separately set for each parameter value range so that the optical attribute can be determined to present the corresponding region of interest differentially.

Optionally, the correspondences set may be stored (Step S930) so that a preset correspondence can be directly acquired when the original image containing a corresponding region of interest is to be presented.

Figure 10:
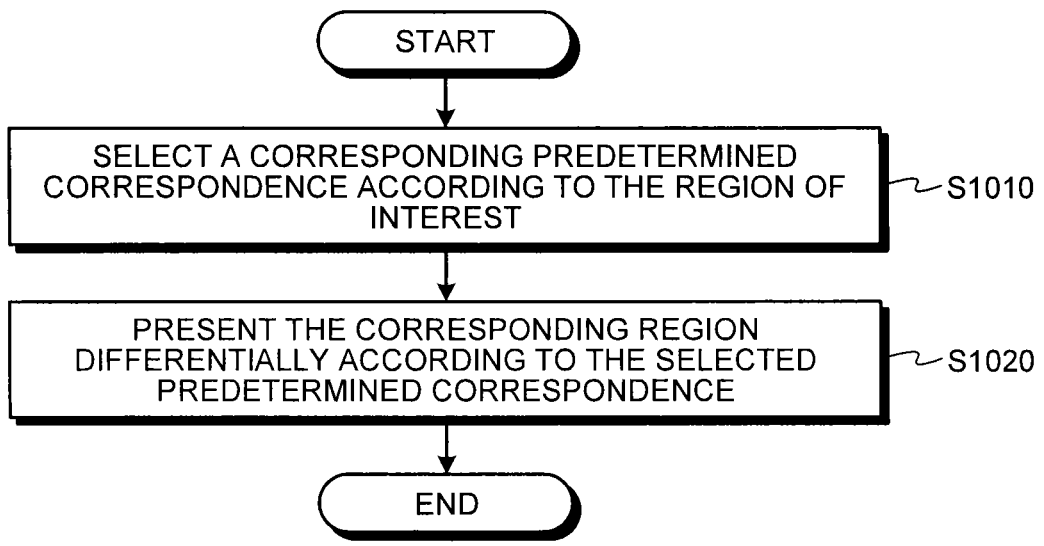
FIG. 10 is a flowchart showing an exemplary processing of using a predetermined correspondence according to a region of interest in an image processing method according to an embodiment of the present invention.

Accordingly, as shown in FIG. 10, if the preset correspondences are stored, the image processing method according to an embodiment of the invention may further include: selecting a corresponding predetermined correspondence according to a region of interest (S1010), and presenting the corresponding region of interest differentially according to the selected predetermined correspondence (S1020).

Further, in a case where the boundaries of the original image and the parametric image do not match with each other, the image processing method according to an embodiment of the invention may further include the step of determining corresponding pixels in the original image and the parametric image by image registration. The image registration may be performed in various specific known ways, which are not described here in detail.

In the image processing method according to embodiments of the invention, the optical attribute values for presenting the original image are determined based on the data value of the original image and the parameter value of the parametric image, thus enabling incorporation of the additional information of the parametric image into the presentation of the original image, so as to present the original image more targetedly, and to achieve a better presentation effect.

Figure 11:
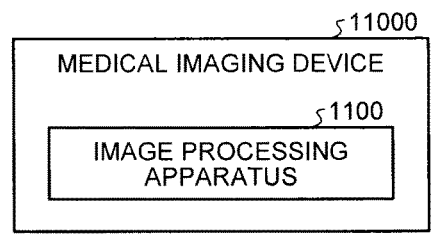
FIG. 11 is a block diagram illustrating an exemplary configuration of a medical imaging device according to an embodiment of the present invention.

A medical imaging device according to another embodiment of the present invention will be described below with reference to the block diagram of FIG. 11. In order to avoid obscuring the spirit and scope of the present invention, other possible members of the medical imaging device are omitted in FIG. 11. The medical imaging device 11000 comprises an image processing apparatus 1100 for acquiring optical attribute values for presenting a medical image so that the medical imaging device 11000 can present the acquired medical image better. The image processing apparatus 1100 may be the image processing apparatus described in any one of the above embodiments. The medical imaging device 11000 may be but not limited to, for example, a magnetic resonance imaging device, an X-ray imaging device, an ultrasonic imaging device, a computed tomography imaging device or a positron emission tomography imaging device.

The image processing apparatus may be arranged in the medical imaging device in a specific way or manner well known by those skilled in the art and is therefore not described in detail herein.

As an example, each step of the aforementioned image processing method and each module and/or unit of the aforementioned image processing apparatus may be implemented as software, firmware, hardware or the combination thereof. In the case where the steps or modules and/or units are realized by software or firmware, a software program for realizing the above-described method is installed in a computer with a specific hardware structure (e.g. the general computer 1200 shown in FIG. 12) from a storage medium or network, and the computer, when installed with various programs, is capable of realizing various functions or the like.

Figure 12:
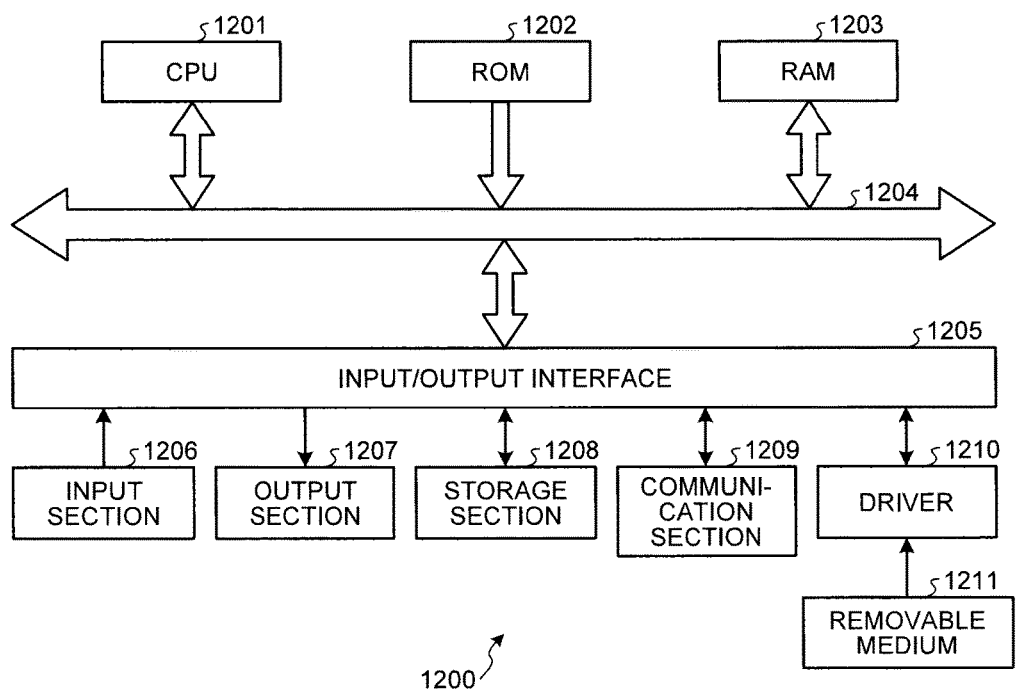
FIG. 12 is a schematic block diagram illustrating the structure of a computer capable of realizing the embodiments/examples of the present invention.

In FIG. 12, an operation processing unit (namely, CPU) 1201 executes various processing according to a program stored in a read-only memory (ROM) 1202 or a program loaded to a random access memory (RAM) 1203 from a storage section 1208. The data needed for various processing of the CPU 1201 may be stored in the RAM 1203 as needed. CPU 1201, ROM 1202 and RAM 1203 are linked with each other via a bus 1204 to which an input/output interface 1205 is also connected.

The following members are linked to the input/output interface 1205: an input section 1206 (including keyboard, mouse or the like), an output section 1207 (including display such as cathode ray tube (CRT), liquid crystal display (LCD), etc., and speaker, etc.), a storage section 1208 (including hard disc or the like), and a communication section 1209 (including a network interface card such as LAN card and modem, etc.). The communication section 1209 performs communication processing via a network such as the Internet. A driver 1210 may also be linked with the input/output interface 1205, if needed. A removable medium 1211, for example, a magnetic disc, an optical disc, a magnetic optical disc, a semiconductor memory or the like, may be installed in the driver 1210 to read a computer program therefrom and install the read computer program in the storage section 1208 as needed.

In the case where the foregoing series of processing is achieved through software, programs forming the software are installed from a network such as the Internet or a storage medium such as the removable medium 1211.

It should be appreciated by those skilled in the art that the storage medium is not limited to the removable medium 1211 shown in FIG. 12, which is distributed separately from the apparatus so as to provide the programs for users. The removable medium 1211 may be, for example, a magnetic disc (including floppy disc (registered trademark)), a compact disc (including compact disc read-only memory (CD-ROM) and digital versatile disc (DVD)), a magneto optical disc (including mini disc (MD)(registered trademark)), and a semiconductor memory. Alternatively, the storage medium may be the hard discs included in ROM 1202 and the storage section 1208, and programs are stored in the storage medium and can be distributed to users along with the storage medium.

The present invention further provides a program product in which machine-readable instruction codes are stored. The image processing method disclosed herein can be implemented when the instruction codes are read and executed by a machine.

Accordingly, a storage medium for carrying the program product in which computer-readable instruction codes are stored is also included in the disclosure of the present invention. The storage medium includes but is not limited to a floppy disc, an optical disc, a magnetic optical disc, a memory card, a memory stick or the like.

In the foregoing description on the specific embodiments of the present invention, the features described and/or shown for an implementation mode may be used in one or more other implementation modes in the same or similar way or combined with those of the other implementation modes, or substitute those of the other implementation modes.

It should be emphasized that the terms 'comprise/include', as used herein, means the existence of a feature, element, step or component in a way not exclusive of the existence or addition of one or more other features, elements, steps or components.

In the above-described embodiments and examples, each step and/or unit is represented with a reference sign consisting of figures. It should be understood by those of ordinary skill of the art that the reference signs are merely intended to facilitate description and drawing but are not to be construed as a limitation on an order or any other aspect.

Furthermore, the method of the present invention is not limited to be performed in the chronological order described herein, and can also be performed in other chronological order, in parallel or independently. Therefore, the implementation orders of the methods described in this specification are not to be construed as a limitation to the scope of the present invention.

Although the present invention has been disclosed with reference to specific embodiments herein, it should be appreciated that all the implementation modes and examples described above are merely illustrative of the present invention but are not to be construed as limiting the present invention. Various modifications, improvements or equivalents can be devised by those skilled in the art without departing from the spirit and scope of the present invention, and such modifications, improvements or equivalents should be considered to be within the scope of the present invention.

What is claimed is:

1. An image processing apparatus, comprising:
a processor configured to
acquire an original image that is an image of an object obtained by a medical imaging device,
acquire a parametric image that is a function image with a specific meaning and is calculated from the original image or that is an image of the object obtained by an imaging method different from that of the original image, and
determine, based on a data value of a pixel of the original image and a parameter value of a corresponding pixel in the parametric image, optical attribute values for presenting the pixel of the original image, wherein
the processor is configured to determine, for at least one optical attribute, based on a predetermined correspondence between a specific parameter value range and a specific optical attribute value, that an area in the original image corresponding to the specific parameter value range has the specific optical attribute value, and display the area in the original image in such a fashion as to distinguish the area from other areas to indicate a region of interest, wherein the correspondence is predetermined based on a type of the parametric image.

2. The apparatus according to claim 1, wherein the predetermined correspondence is defined by a transfer function, the transfer function taking the data value and the parameter value as input and the optical attribute values as output.

3. The apparatus according to claim 1, wherein the processor is configured to determine, in an area in the original image corresponding to the same parameter value range, a specific optical attribute value for a sub-area corresponding to a specific data value range of the original image so as to distinguish the sub-area.

4. The apparatus according to claim 1, wherein the processor is configured to
divide parameter values into two or more ranges, and
set the correspondence separately for each parameter value range so that the optical attribute values are determined to differentially present an area corresponding to the parameter value range.

5. The apparatus according to claim 1, wherein the processor is configured to perform an image registration to determine corresponding pixels in the original image and the parametric image.

6. The apparatus according to claim 1, wherein the processor is configured to acquire the parametric image obtained by performing numerical calculation on the original image.

7. The apparatus according to claim 6, wherein the processor is configured to
acquire a magnetic resonance image of the object,
acquire a fractional anisotropy image corresponding to the magnetic resonance image, and
determine the optical attribute values to highlight an area corresponding to a parameter value of grey matter or white matter.

8. The apparatus according to claim 6, wherein the processor is configured to
acquire a magnetic resonance image of the object,
acquire a chemical shift image corresponding to the magnetic resonance image, and
determine the optical attribute values to highlight an area corresponding to a parameter value of a tumor area.

9. The apparatus according to claim 6, wherein the processor is configured to
acquire a diffusion-weighted image corresponding to a magnetic resonance image, and
determine the optical attribute values to highlight an area corresponding to a parameter value of a cerebral infarction area.

10. The apparatus according to claim 1, wherein the processor is configured to acquire the parametric image obtained by the imaging method different from that of the original image.

11. The apparatus according to claim 1, wherein the processor is configured to determine a color, grayscale or transparency for presenting the pixel of the original image.

12. The apparatus according to claim 1, wherein the processor is configured to acquire an X-ray image, ultrasonic image, computed tomography image, magnetic resonance image or positron emission tomography image of the object.

13. The apparatus according to claim 1, wherein the processor is configured to determine the optical attribute values for presenting the pixel of the original image according to a type of the original image.

14. The apparatus according to claim 1, wherein the processor is configured to determine the optical attribute values of the pixel in the original image according to the data value of the pixel in the original image and parameter values of a plurality of pixels in the parametric image.

15. An image processing method, comprising:
acquiring an original image that is an image of an object obtained by a medical imaging device;
acquiring a parametric image that is a function image with a specific meaning and is calculated from the original image or that is an image of the object obtained by an imaging method different from that of the original image;
determining, based on a data value of a pixel of the original image and a parameter value of a corresponding pixel in the parametric image, optical attribute values for presenting the pixel of the original image, wherein
the determining includes determining, for at least one optical attribute, based on a predetermined correspondence between a specific parameter value range and a specific optical attribute value, that an area in the original image corresponding to the specific parameter value range has the specific optical attribute value; and
displaying the area in the original image in such a fashion as to distinguish the area from other areas to indicate a region of interest, wherein the correspondence is predetermined based on a type of the parametric image.

16. A medical imaging device, comprising:
an image processing apparatus that includes a processor configured to
acquire an original image that is an image of an object obtained by a medical imaging device,
acquire a parametric image to that is a function image with a specific meaning and is calculated from the original image or that is an image of the object obtained by an imaging method different from that of the original image, and
determine, based on a data value of a pixel of the original image and a parameter value of a corresponding pixel in the parametric image, optical attribute values for presenting the pixel of the original image, wherein
the processor is configured to determine, for at least one optical attribute, based on a predetermined correspondence between a specific parameter value range and a specific optical attribute value, that an area in the original image corresponding to the specific parameter value range has the specific optical attribute value, and
display the area in the original image in such a fashion as to distinguish the area from other areas to indicate a region of interest, wherein the correspondence is predetermined based on a type of the parametric image.

17. The medical imaging device according to claim 16, wherein
the predetermined correspondence is defined by a transfer function, the transfer function taking the data value and the parameter value as input and the optical attribute values as output, and
the processor is configured to
acquire the parametric image obtained by performing numerical calculation on the original image,
acquire a magnetic resonance image of the object,
acquire a chemical shift image corresponding to the magnetic resonance image, and
determine the optical attribute values to highlight an area corresponding to a parameter value of a tumor area.

* * * * *